United States Patent [19]

Kako et al.

[11] Patent Number: 5,374,814
[45] Date of Patent: Dec. 20, 1994

[54] CASH TRANSACTION MACHINE AND METHOD WITH MONEY DISINFECTION

[75] Inventors: Yutaka Kako, Nagoya; Asahiko Isobe, Tokyo; Masataka Kawauchi, Ishioka; Tomomi Mizuno, Aichi; Teruaki Mitsuya, Katsuta, all of Japan

[73] Assignee: Hitachi, Ltd., Tokyo, Japan

[21] Appl. No.: 637,785

[22] Filed: Jan. 7, 1991

[30] Foreign Application Priority Data

Jan. 12, 1990 [JP] Japan ........................... 2-3585
Sep. 3, 1990 [JP] Japan ......................... 2-233017

[51] Int. Cl.5 .............................. G06F 15/30
[52] U.S. Cl. ............................ 235/379; 902/12; 209/534
[58] Field of Search ............ 235/379; 902/12; 209/534

[56] References Cited

U.S. PATENT DOCUMENTS

| 4,449,050 | 5/1984 | Kamhi | 250/455.11 |
| 4,697,071 | 9/1987 | Hiraoka et al. | 902/12 |
| 4,972,958 | 11/1990 | Ito et al. | 902/12 |
| 5,021,639 | 6/1991 | Hara et al. | 235/379 |

FOREIGN PATENT DOCUMENTS

| 58-124873 | 8/1983 | Japan . | |
| 47260 | 2/1988 | Japan | 209/534 |
| 92566 | 4/1988 | Japan | 209/534 |

*Primary Examiner*—John Shepperd
*Attorney, Agent, or Firm*—Antonelli, Terry, Stout & Kraus

[57] ABSTRACT

Cash transaction machine and method for receiving and/or dispensing money by user's manipulation to transact the money includes a bill receptacle, a bill dispense port, a bill storage and a transport unit for transporting the bill between the receptacle and/or the dispense port, a disinfection unit, and the storage. The bills received and/or to be dispensed are disinfected by the disinfection unit arranged in the transport unit by heating the bills by a heated roller, irradiating the bills by an ultraviolet ray from an ultraviolet ray lamp or applying disinfecting liquid to the bills. Alternatively, the bills are disinfected by a disinfection unit arranged in the storage by heating the bills by a heater or irradiating an electromagnetic wave to the bills.

15 Claims, 6 Drawing Sheets

CASH TRANSACTION MACHINE AND METHOD WITH MONEY DISINFECTION

BACKGROUND OF THE INVENTION

The present invention relates to the cash transaction machine, and a more particularly to cash transaction machine and method for receiving cash (bills and coins) thrown in by a user of an automatic teller machine, an automatic charge paying machine or an automatic vending machine, transacting it by user's manipulation and redispensing cash as required.

In an automatic teller machine shown in JP-A-62-42296, the machine receives cash (bills and coins) thrown in by a user, transacts (receives) it by the user's manipulation and stores it in a bill storage box. It also transacts (pays) cash by the user's manipulation, takes bills out of the bill storage box and dispenses them to the user. In an automatic vending machine or an automatic ticketing machine, it receives cash thrown in by a user, transacts (dispenses commodities or issues a tcket) by th user's manipulation, and dispenses change as required. In those machines, the cash thrown in by the users are discharged as dispensing cash or change. Accordingly, dirty bills or coins may be included in the dispensed cash.

Money is transferred from many sources of people to other people and it is sometimes desired to clear the dirty money for the users or the manager of the machine. JP-A-47-45997, JP-A-49-24194 and JP-A-63-66059 disclose machines which sterilize and disinfect bills, but those are exclusively used for the sterilization and disinfection. Thus, in order to sterilize and disinfect the bills, the manager of the machine must handle the dirty bills and put them into the machine. Accordingly, it is not possible to automatically sterilize and disinfect the money without intervention of the manager in a machine such as the cash transaction machine which receives the cash thrown in by the user, transacts it by the user's manipulation, and redischarges the thrown-in cash as dispensing money or change.

SUMMARY OF THE INVENTION

It is an object of the present invention to provide cash transaction machine and method which has a money disinfection function.

It is another object of the present invention to impart a good impression to users and a manager of a cash transaction machine by disinfecting moneys received and paid in the transaction in order to maintain the money in good sanitary condition.

In order to achieve the above objects, the cash transaction machine for receiving and/or dispensing money by user's manipulation comprises: a receptacle for receiving and/or dispensing the money; a storage for the money; transport means for transporting the money between the receptacle and the storage; and disinfection means for disinfecting the money received and/or to be dispensed.

Further, the cash transaction machine of the present invention having disinfection means for heating money during transport to disinfect the money, the disinfection means includes first transport means including heat means for heating money, for transporting the money, and second transport means including an endless belt and the second transport means facing said first transport means for holding the money therebetween to transport the money.

The cash transaction method of the present invention includes the steps of: receiving money from a receptacle; transporting the money by a transport unit; disinfecting the money by a disinfection unit arranged in said transport unit during the transportation of the money; storing the transported money in a storage; and dispensing money from a discharge port by user's manipulation.

Further, the cash transaction method of the present invention includes the steps of: receiving money from a receptacle; transporting the money by a transport unit; storing the transported money in a storage; disinfecting the money by a disinfection unit arranged in the storage; and dispensing the money from a discharge port by user's manipulation.

In the cash transaction machine of the present invention, the bills received from the receptacle are disinfected by the disinfection unit during the transportation by the transport unit or the store in the storage. In this manner, the bills dispensed from the cash transaction machine are kept in a better sanitary condition than that of the received bills.

In the cash transaction machine which transports the bills in the machine at a high speed, the disinfection unit includes first transport means having a heating unit built therein and second transport means including an endless belt. A wrap angle around which the first transport means and the second transport means contact is selected large so that a large contact angle is attained to heat the bills for a longer time.

BRIEF DESCRIPTION OF THE DRAWINGS

These and other objects and advantages of the present invention will become apparent by reference to the following description and accompanying drawings wherein.

DESCRIPTION OF THE PREFERRED EMBODIMENTS

One embodiment of the present invention is now explained in detail with reference to the drawings.

Figure 1:
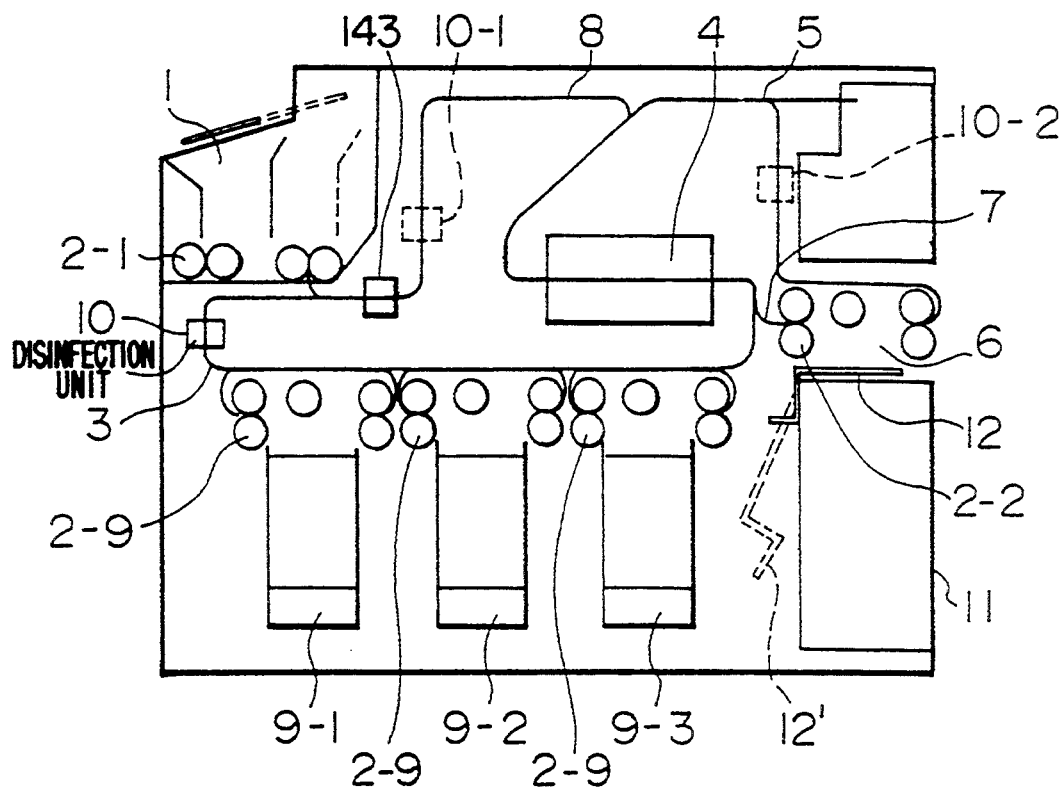
FIG. 1.shows a schematic view of an automatic teller machine in accordance with one embodiment of the present invention.

FIG. 1 shows an automatic teller machine in accordance with one embodiment of the present invention. The bills thrown in from a receptacle 1 are separated one by one by a separation unit 2-1 and they are transported to a discrimination unit 4 by a transport unit 3. The discrimination the unit 4 discriminates denomination, genuineness, the damage and the number of sheets. They are further transported by a transport unit 5 and stored in a temporary store unit 6. If the transaction manipulated by a user is met, the bills are separated by a separation unit 2-2, transported by a transport unit 7 to the discrimination unit 4 for discrimination, and transported to and stored in denomination boxes 9-1, 9-2 and 9-3 which store the bill by denomination, through transport units 8 and 3. This is the money receiving transaction.

In the money paying transaction, the required numbers of sheets of bills are separated from the denomination boxes 9-1, 9-2 and 9-3 by a separation unit 2-9, they are stacked in the receptacle 1 and dispensed.

In the present embodiment of the automatic teller machine, the receptacle 1 is shared by a money receiving port and a money paying port, although a coin throw-in port and a charge port may be separated as they are in an automatic ticketing machine.

When the bills residing in the denomination boxes 9-1, 9-2 and 9-3 become small because the money paying transaction is larger than the money receiving transaction, bills are loaded in a removable/insertable bill cassette 11; a separator 12 is retracted to a broken line position 12', and the bills in the cassette 11 are removed by the temporary store unit 6. The bills are transported to the discrimination unit 4 through the transport unit 7; the discrimination unit 4 discriminates the denomination and the numbers of sheets of the bills, and the bills are stored in the denomination boxes 9-1, 9-2 and 9-3 through the transport units 8 and 3.

On the other hand, when the money receiving transaction is larger that the money paying transaction and one of the denomination boxes 9-1, 9-2 and 9-3 becomes full; the bills are taken out of the full denomination box, discriminated by the discrimination unit 4 for denomination and the number of sheets, and stored into the cassette 11. All bills may be collected to check the balance of the bills in the machine. The balance of the bills in the machine may also be checked while they are sequentially transported into the denomination boxes 9-1, 9-2 and 9-3 and the bill cassette 11 through the discrimination unit 4.

In FIG. 1, a disinfection unit 10 is provided on the path of the transport unit 3. The disinfection unit 10 disinfects (including sterilization and pasteurization) the bills transported by the transport unit 3. FIGS. 2 to 10 show specific embodiments of the disinfection unit 10.

Figure 2:
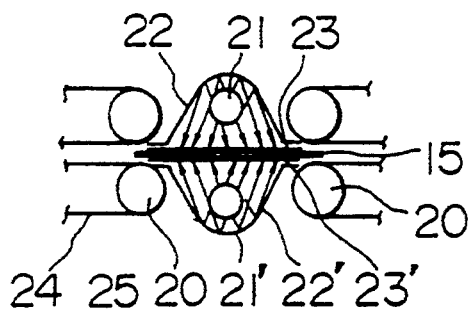
FIGS. 2 to 5 show schematic views of disinfecting devices which disinfects moneys during the transportation, in which FIG. 2 uses an ultraviolet ray, FIG. 3 uses a heated roller, FIG. 4 uses disinfecting liquid and FIG. 5 uses ozone as disinfection agent.

In FIG. 2, an electromagnetic wave is irradiates the bills to disinfecting them. In the present embodiment, the disinfection unit (disinfection device) comprises a pair of ultraviolet ray lamps 21 and 21' arranged vertically relative to the transport unit in the path of the transport unit 20 which includes a belt 24 and a roller 25, reflection mirrors 22 and 22' arranged to cover the lamps 21 and 21', and guides 23 and 23' for holding the bills.

The ultraviolet rays from the lamps 21 and 21' irradiate both sides of the bill 15 transported one at a time by the transport unit 20 so that the bill are disinfected. A wavelength of the ultraviolet ray is selected to be most effective again the bacteria on the bills to be sterilized and disinfected.

While the ultraviolet ray is utilized in FIG. 2, other electromagnetic wave which have the disinfection function (including sterilization and pasteurization) such as microwave, X ray and ultrasonic wave may be employed. When the electromagnetic wave is harmful to the human body such as ultraviolet ray or X ray is used, the disinfection unit 10 is shielded.

Figure 3:
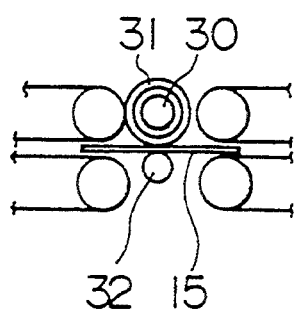

FIG. 3 shows an embodiment which heats the bill for the disinfection. In the present disinfection unit, the bill 15 is pressed to a heated roller 31 made of hard material such as metal having a heater 30 built therein, by a pressure roller 32 made of flexible material such as resin to disinfect (including sterilization and pasteurization) the bill. The heated roller is temperature-controlled by a temperature controller (not shown). The temperature of the heated roller is preferably high for the purpose of sterilization but is set below a burning temperature of the bill in order to prevent the deformation and burning of the bill. In the present embodiment, it is set to 220° to 240° C.

Figure 4:
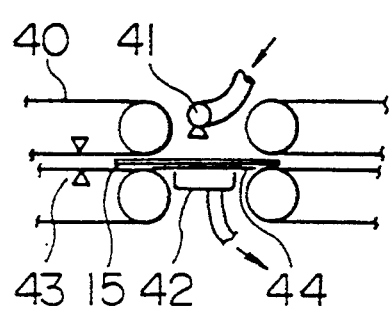

FIG. 4 shows an embodiment which disinfects the bill by drugs. The disinfection unit of the present embodiment comprises a money sensor 43 (to be described in detail later) mounted on the transport unit, a nozzle 41 connected to a drug supply source (not shown) for discharging the drugs, a drug recovery unit 42 and a guide 44 for holding the money. When the transport of the money is detected by the money sensor 43, the drugs are discharged to the money 15 from the nozzle 41 to disinfect the money. The drugs are recovered by the recovery unit 42 and returned to the supply source. The recovery unit is effective particularly when the drugs are harmful to the human body. It may be omitted when the drugs are not harmful to the human body.

Figure 5:
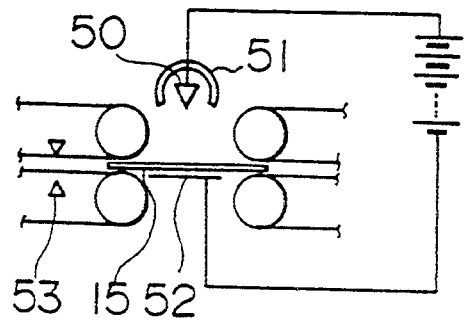

FIG. 5 shows an embodiment which disinfect the bill by ozone. The disinfection unit of the present embodiment comprises an electrode 50 connected to a positive pole, a cover 51 for the electrode 50 and a cathode 52 facing the electrode 50. A voltage is applied to the electrode 50 to generate ozone, and when the bill 15 is transported under the electrode, ozone is showered to disinfect the bill. This unit can be readily constructed.

FIGS. 6 to 10 show embodiments of the disinfection unit which can be suitably used in a cash transaction machine which transports bills in the machine at a high speed. In the automatic teller machine, 8 to 10 bills per second are received or dispensed. To this end, it is necessary to transport the bill at a velocity of 1 m/sec. In the embodiment of FIG. 3, if the bill is transported at such a velocity, the time for which the bill contacts to the heated roller is short so that it is difficult to heat the bill to the required temperature and keep the bill at that temperature. The embodiments of the disinfection unit which attain a sufficient heating effect in such a machine are described below.

Figure 6:
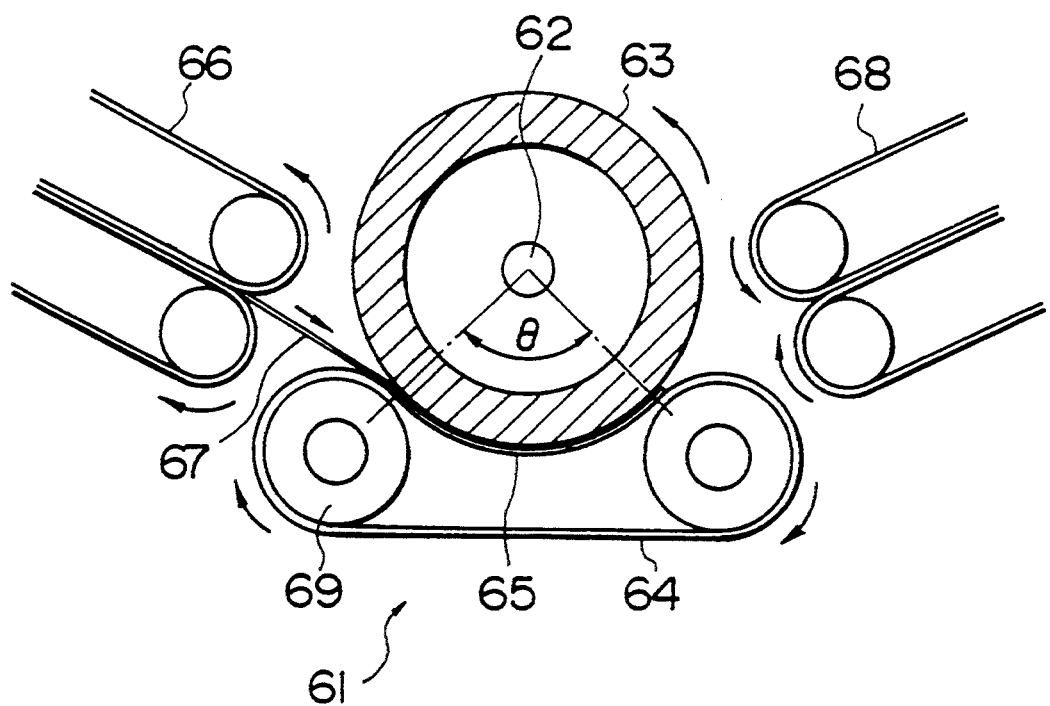
FIGS. 6 to 10 show schematic views of disinfecting devices which are used when moneys are transported at a high speed, in which FIG. 6 uses an endless belt to assure a long contact length, FIG. 7 uses a heater on an endless belt, FIG. 8 uses a pair of endless belts, FIG. 9 uses a water supply device and FIG. 10 uses an ultraviolet ray.

FIG. 6 shows an embodiment of a bill disinfection unit of the present invention.

The unit 61 of the present embodiment comprises a heated roller 63 including a metal roller having a halogen lamp 62 as heating means built therein and a rubber belt 64 supported by two pulleys 69. An appropriate tension is imparted to the rubber belt 64 so that it is pressed to the heated roller 63. It contacts to the heated roller 63 to wrap around it. A contact area of the heated roller 63 and the rubber belt 64 is a bill heating unit 65. The heated roller 63 and the rubber belt 64 rotate to transport the bill fed into the heating unit 65.

An operation of the present embodiment is described below.

The bill 67 fed to the disinfection unit 61 by the transport means 66 at the entry is fed into the contact area of the heated roller 63 and the rubber belt 64, that is, the heating unit 65. The bill 67 is held between the high temperature heated roller 63 and the rubber belt 64 and transported through the heating unit 65 by the rotation of the rubber belt 64 and the heated roller 63 while it is heated thereby, and discharged to the exit transport means 68 from the heating unit 65.

In the present embodiment, a wrap angle ($\theta$) around which the heated roller 63 and the rubber belt 64 contact is selected large so that a large contact length, that is, a long contact time is assured and a large disinfection and sterilization effect is attained.

In the disinfection unit 61 of the present embodiment, the bill is disinfected and sterilized by heating and pressing the bill, and the folds and the rumples of the bill are removed. Further, the handling in the automatic cash transaction machine is easy.

Figure 7:
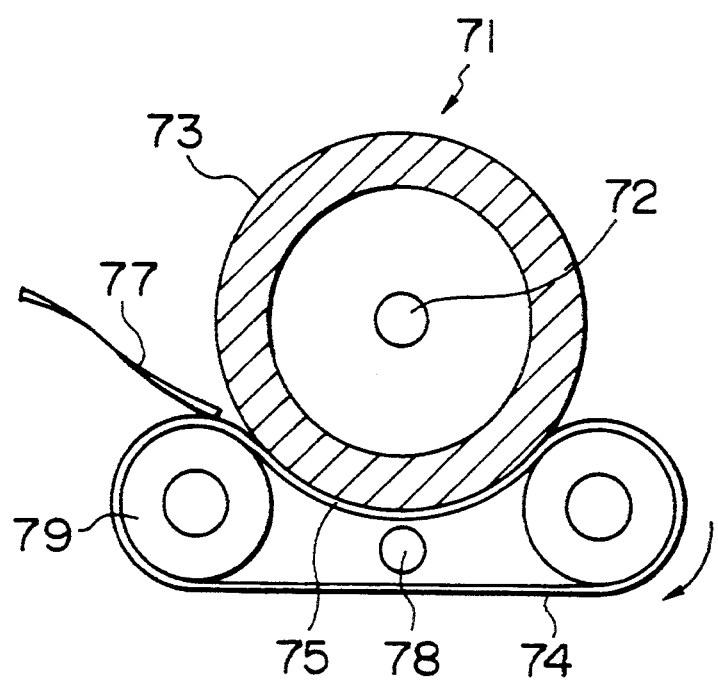

FIG. 7 shows other embodiment 71 of the present invention. In addition to the unit 61 of the embodiment of FIG. 6, a halogen lamp 78 is provided to face a pressure belt 74 as second heating means. In the unit 71 of the present embodiment, the bill 77 is heated in a shorter time so that a larger disinfection and sterlization effect is attained.

Figure 8:
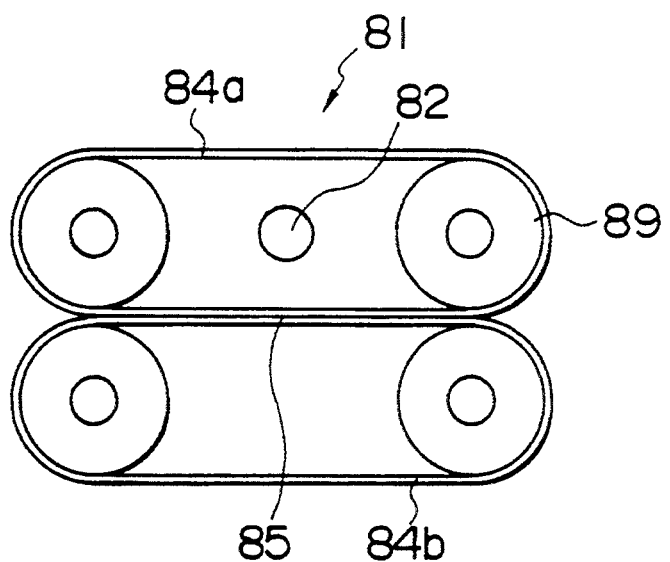

FIG. 8 shows other embodiment 81 of the present invention. In place of the heated roller 63 of the unit 61 of the embodiment shown in FIG. 6, a belt 84a is provided, and a bill 87 is held between the two belts 84a and 84b and transported thereby. A halogen lamp may be additionally arranged to face the belt 84b. In the present embodiment, the freedom of the shape and length of the heating unit 85 is increased.

Figure 9:
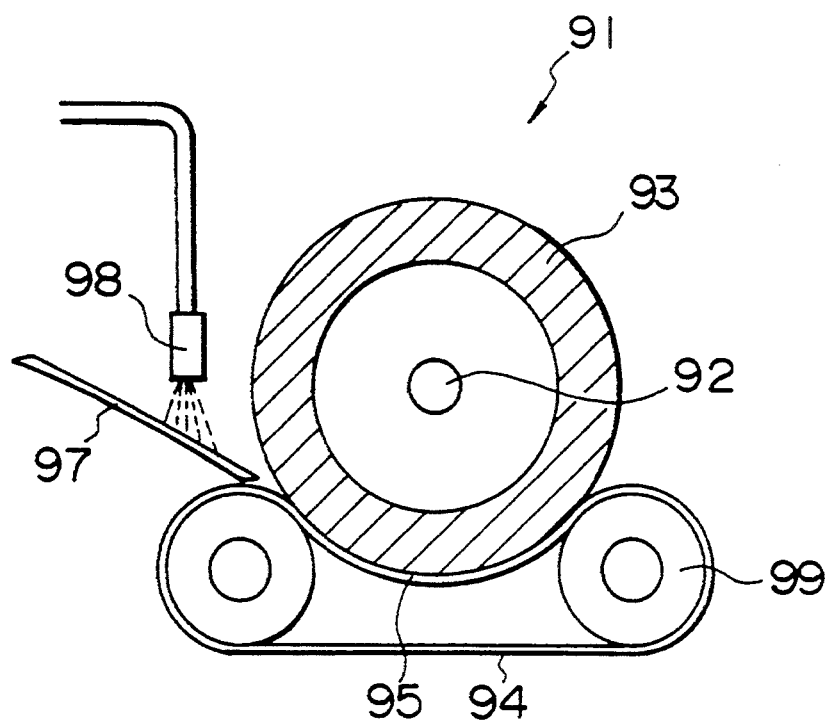
Figure 10:
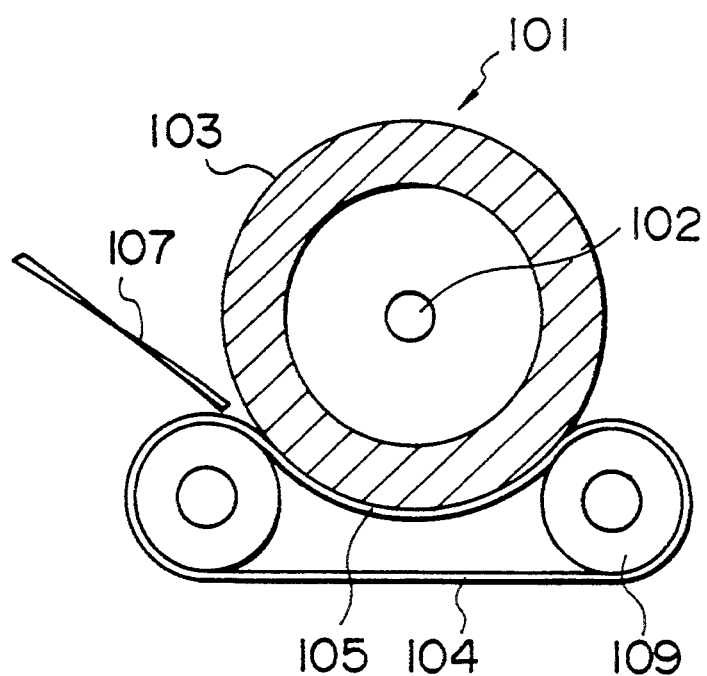

FIGS. 9 and 10 show other embodiments of the present invention. In a unit 91 of the embodiment shown in FIG. 9, a nozzle 98 for discharging water is arranged at the entry of the heating unit 65 of the unit 61 of the embodiment shown in FIG. 6. In a unit 101 of the embodiment shown in FIG. 10, a mercury lamp 102 is used in place of the heating halogen lamp 62 of the unit 61 of the embodiment shown in FIG. 6, and a heated roller 103 is made of a transparent material.

In the unit 91 of the embodiment shown in FIG. 9, the bill 97 fed into the heating unit 95 is applied with water by the nozzle 98 and then heated by the heating unit 95. As a result, the applied water is converted to high temperature water steam which disinfects and sterilizes the bill 97. In the unit 101 of the embodiment shown in FIG. 10, the heated roller 103 is made of silica having a high ultraviolet ray transmittance and the mercury lamp 102 having a high ultraviolet ray emission rate is provided in the heated roller 10. Accordingly, the bill 107 is exposed to the high temperature as well as a strong ultraviolet ray. As a result, the bill 107 is highly disinfected and sterilized.

Figure 11:
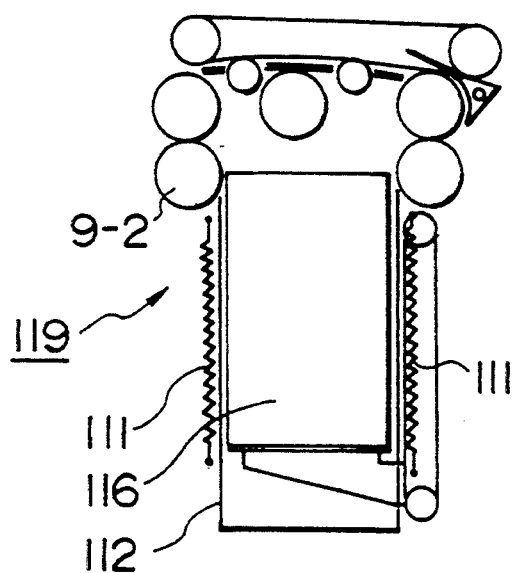
FIGS. 11 to 13 show schematic views of embodiments which disinfect moneys in denomination boxes, in which FIG. 11 uses a heater for heating, FIG. 12 uses electromagnetic wave irradiation for heating and FIG. 13 uses gas for disinfection.

An embodiment which has a disinfection unit in a denomination box is now explained. In the embodiment shown in FIG. 1, the disinfection unit is arranged in the transport unit 3. In the present embodiment, the disinfection units are arranged in the denomination boxes 9-1, 9-2 and 9-3 so that the bills are disinfected (including sterilization and pasteurization) while the bills are stored in the denomination boxes. FIG. 11 shows a specific embodiment. A heater 111 is arranged around a bill storage 112 of a denomination box 119 to heat the stored bills 116 in order to disinfect the bills.

Figure 12:
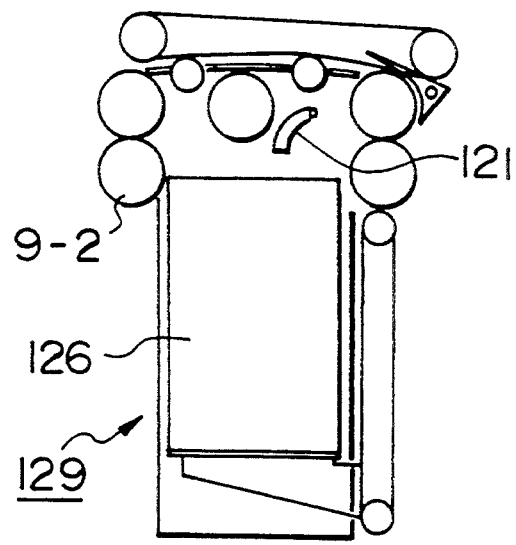

FIG. 12 shows an embodiment which heats the bills in a different manner. In the present embodiment, a microwave irradiation port 121 connected to a magnetron (not shown) is arranged on a denomination box 129 so that a microwave irradiates the bills 126 to heat and disinfect the bills. In FIG. 11, the bills are heated by the heater, and in FIG. 12, the bills are heated by the microwave. The heating method is not limited to those but, additionally, hot air may be blown into the denomination box, for example.

Figure 13:
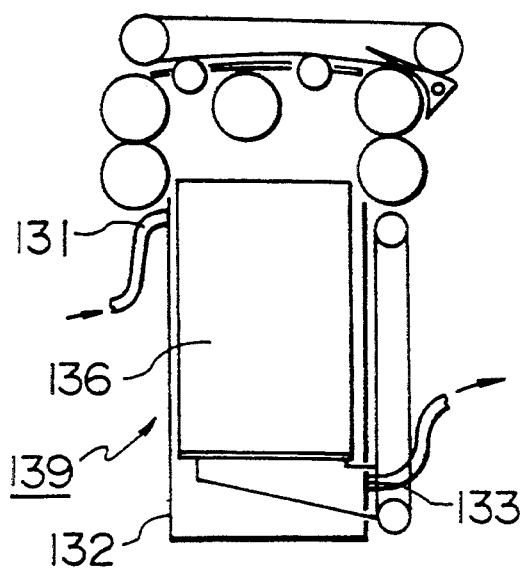

FIG. 13 shows another embodiment which disinfects (including sterilization and pasteurization) the bills while the bills are stored in the denomination box. A gas supply port 131 connected to a gas supply source (not shown) is provided in a storage 132 to fill the gas in the denomination box and the gas which is effective to disinfect the bills 136 reacts with the bills. In the present embodiment, like in the embodiment shown in FIG. 4, gas recovery means may be provided to recover the gas filled in the storage to the gas supply source through the gas recovery port 136.

The disinfection means described above may have a bill deodorization effect by selecting the means and condition to lower or stop the biochemical action which causes the bad smell.

Figure 14:
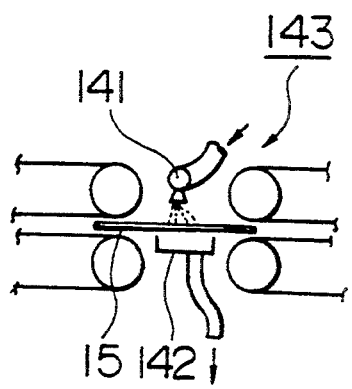
FIG. 14 shows a schematic view of an embodiment of a smell imparting device which gives smell to the money.

The automatic teller machine of FIG. 1 is provided with means 143 for imparting smell to the bills. FIG. 14 shows a specific embodiment for imparting smell. A nozzle 141 is provided closely to the transport path of the transport unit and volatile perfume is applied to the bills 15 from a supply source (not shown). By applying the volatile perfume to the bill 15 when it is transported to the receptocle 1, the smell may be imparted to the bill. Extra perfume is recovered by recovery means 142 and returned to the supply source.

In the above embodiments, the disinfection unit is arranged at the position shown in FIG. 1, but the disinfection (including sterilization and pasteurization) of moneys is effected in the following transactions (1) to (3).

(1) The bills thrown into the receptacle 1 are taken in, discriminated by the discrimination unit 4 and stored in the temporary store 6.
(2) The bills are taken out of the temporary store 6 after the above transaction, discriminated by the discrimination unit 4 and stored into the denomination box 9-1.
(3) The bills loaded in the cassette 11 are taken out by the temporary store 6, discriminated by the discrimination unit 4, and stored in the denomination box 9-1.

The disinfection unit may be arranged at the position of 10-1 in FIG. 1. In this case, the disinfection is effected when;

(4) the bills are taken out of the denomination boxes 9-1, 9-2 and 9-3, discriminated by the discrimination unit 4 and stacked in the receptacle 1, and
(5) the money receiving transaction (2) and the supplement/load transaction (3) described above.

The disinfection unit may be arranged at the position 10-2 in FIG. 1. In this case, the disinfection is effected when;

(6) the bills are taken out of the denomination boxes 9-1, 9-2 and 9-3, discriminated by the discrimination unit 4 and stored into the cassette 11, and (7) the money counting transaction (1) described above.

The disinfection (including sterilization and pasturization) means described above may be provided at any one of the positions 10, 10-1 and 10-2 in FIG. 1, or at any two positions or at three positions. The object of the present invention can also be achieved when they are provided at other position. The timing of the disinfection of the moneys may be in one of the transactions (1) to (7) or in a plurality of transactions. The moneys may also be disinfected during the checking of the moneys.

Figure 15:
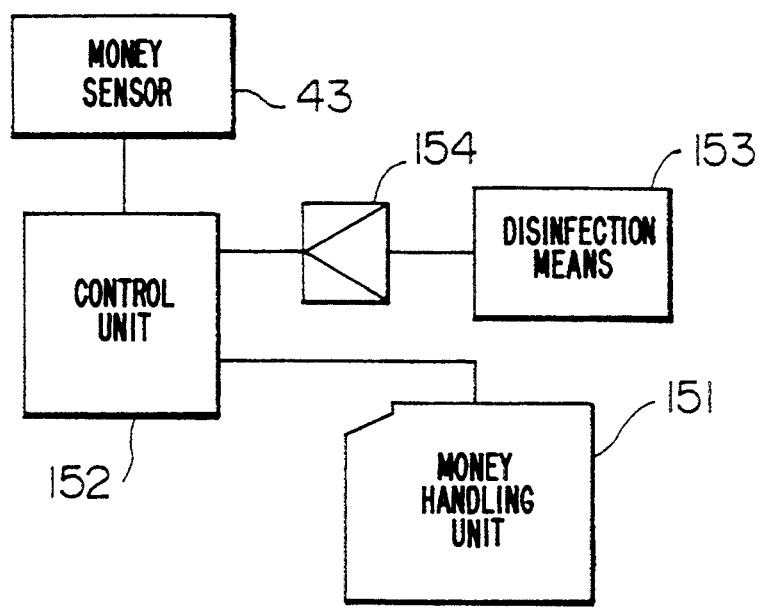
FIGS. 15 and 16 show block diagrams of a control unit which controls the machine of the present invention.

FIG. 15 shows a block diagram for explaining the control in the embodiment of the present invention. The bill handling unit 151 shown in FIG. 1 is controlled by a control unit 152, as it is in the exiting machine. The money disinfection means 153 is connected to the control unit 152 through a drive unit 154. The control unit 152 determines the start and stop timings of the disinfection means 153 in accordance with the transaction done by the money handling unit 151, the amount of bills stored, elapsed time and environmental conditions, and drives the disinfection means through the drive unit 154 in a manner to maximize the effect.

In order to attain full effect of the disinfection means which uses the ultraviolet ray lamp or the heated roller shown in FIGS. 2, 3 and 6 to 10, preheating may be required. The control unit 152 may always drive the heat supply source or drive it in response to the start of transaction caused by the user's manipulation.

In the embodiments of FIGS. 4 and 5 in which the ozone or drugs are applied, the disinfection unit is driven in timed relation with the transport of moneys. For example, as shown in FIG. 4, the money sensor 43 is arranged in front of the nozzle 41, the money detection signal from the money sensor 43 is sent to the control unit 152, which drives in response thereto.

Figure 16:
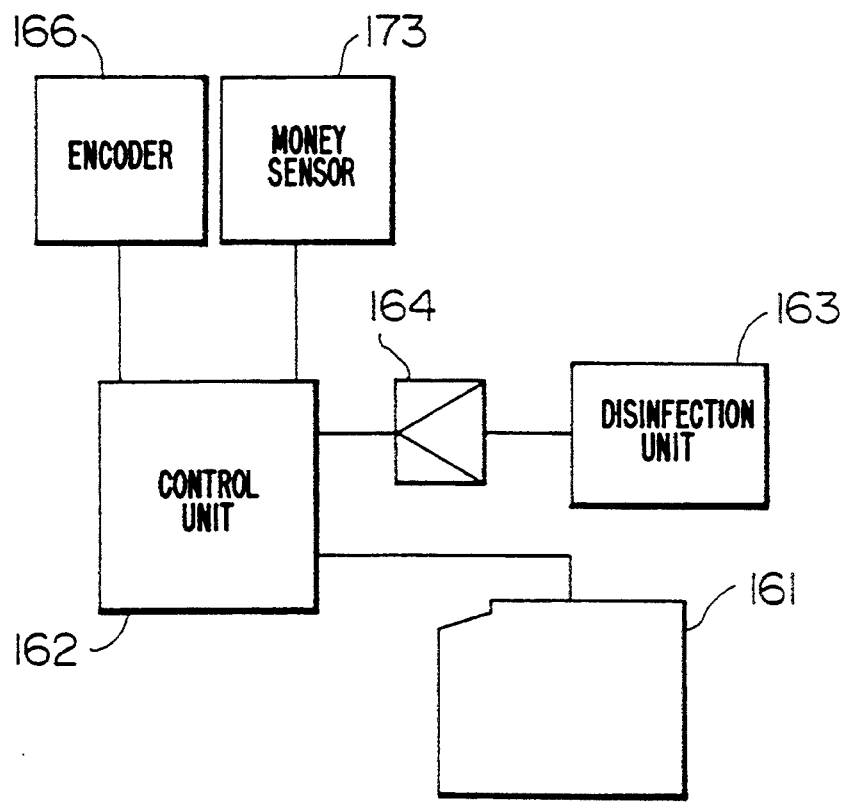

FIG. 16 shows a diagram for explaining another embodiment of the control. In the present embodiment, a money sensor 173 for detecting the passage of the money and an encoder 166 for encoding a displacement along the transport path are provided in the discrimination unit 4. When the money passes through the discrimination unit 4, the time of passage of the money is informed to the control unit 162 by the money sensor 173. The encoder 166 sends the encode signal so that the control unit determines the position of the transport path along which the money is transported and drives the disinfection unit 163 through the drive unit 164 in the timed relation with the passage of the money through the disinfection unit.

In the embodiments of FIGS. 11 and 12 in which the disinfection is effected in the denomination box, the disinfection unit may be always driven or driven periodically by a timer of the control unit.

The disinfection of the bills have been explained in the above embodiments, although the unit of the present invention is also applicable to coins. It may also be widely applicable to other than automatic teller machines such as automatic vending machine and automatic ticketing machine. The present invention is also applicable to the disinfection sterilization and pasteurization of other than bills, such as sheets.

While particular embodiments of the present invention have been shown and described, it will be obvious to those skilled in the art that various changes and modifications may be made without departing from the present invention in its broader aspects.

What is claimed is:

1. A cash transaction machine for receiving and/or dispensing money by user's manipulation, comprising:
   a receptacle for receiving and/or dispensing the money;
   a storage of the money;
   transport means for transporting the money between said receptacle and said storage; and
   disinfection means for disinfecting the money received and/or to be dispensed, and
   wherein said disinfection means is provided in said storage to disinfect the money during the store in said storage.

2. A cash transaction machine according to claim 1 wherein said disinfection means irradiates an electromagnetic wave to the money.

3. A cash transaction machine according to claim 1 wherein said disinfection means heats the money.

4. A cash transaction machine according to claim 1 wherein said disinfection means introduces disinfecting gas into said storage.

5. A cash transaction machine for receiving and/or dispensing money by user's manipulation, comprising:
   a receptacle for receiving and/or dispensing the money;
   a storage of the money;
   transport means for transporting the money between said receptacle and said storage; and
   disinfection means for disinfecting the money received and/or to be dispensed, and
   wherein said disinfection means is provided in said transport means to disinfect the money during the transportation by said transport means, and
   wherein said disinfection means irradiates an electromagnetic wave to the money.

6. A cash transaction machine for receiving and/or dispensing money by user's manipulation, comprising:
   a receptacle for receiving and/or dispensing the money;
   a storage of the money;
   transport means for transporting the money between said receptacle and said storage; and
   disinfection means for disinfecting the money received and/or to be dispensed, and
   wherein said disinfection means is provided in said transport means to disinfect the money during the transportation by said transport means, and
   wherein said disinfection means injects ozone to the money.

7. A cash transaction machine for receiving and/or dispensing money by user's manipulation, comprising:
   a receptacle for receiving and/or dispensing the money;
   a storage of the money;
   transport means for transporting the money between said receptacle and said storage; and
   disinfection means for disinfecting the money received and/or to be dispensed, and
   wherein said disinfection means is provided in said transport means to disinfect the money during the transportation by said transport means, and
   wherein said disinfection means applies drugs to the money.

8. A cash transaction machine for receiving and/or dispensing money by user's manipulation, comprising:

a receptacle for receiving and/or dispensing the money;

a storage of the money;

transport means for transporting the money between said receptacle and said storage; and disinfection means for disinfecting the money received and/or to be dispensed, and wherein said cash transaction machine further comprises smell imparting means for imparting smell to the money.

9. A cash transaction machine having disinfection means for heating money during transport to disinfect the money, the disinfection means comprising;

first transport means including heat means for heating money, for transporting the money, and second transport means including an endless belt and facing said first transport means for holding the money therebetween to transport the money.

10. A cash transaction machine according to claim 12 wherein said second transport means includes heat means for heating the money.

11. A cash transaction machine according to claim 9 wherein said first transport means includes an endless belt.

12. A cash transaction machine according to claim 9 further comprising water application means for applying water to the money, wherein the money is heated by said heat means and the applied water is converted to water vapor to disinfect the money.

13. A cash transaction machine according to claim 9 wherein said first transport means is made of a high ultraviolet ray transmittance material, and an ultraviolet ray generator is built in said first transport means.

14. A cash transaction method comprising the steps of:

receiving money from a receptacle;

transporting the money by a transport unit;

storing the transported money in a storage;

disinfecting the money by a disinfection unit arranged in the storage; and dispensing the money from a discharge port by user's manipulation.

15. A cash transaction machine for receiving or dispensing money by manipulation of a user, comprising:

a receptacle for receiving or dispensing the money;

a storage of the money;

transport means for transporting the money between the receptacle and the storage; and disinfection means for disinfecting the money received or to be dispensed, and wherein the disinfection means is provided in the transport means to disinfect the money during the transportation by the transport means by heating the money between 220° to 240° C.

* * * * *